United States Patent [19]

DesLauriers et al.

[11] Patent Number: 5,774,563
[45] Date of Patent: Jun. 30, 1998

[54] COMBINED ELECTRONIC ACOUSTICAL STETHOSCOPE

[76] Inventors: Richard J. DesLauriers, 78 Joseph St., Waterbury, Conn. 06705; James M. Muskatello, 51 W. Pines Dr., Southington, Conn. 06489

[21] Appl. No.: 680,274

[22] Filed: Jul. 11, 1996

[51] Int. Cl.[6] ........................................................ A61B 7/04
[52] U.S. Cl. ................................................................ 381/67
[58] Field of Search ............................. 381/67; 181/131; 128/715

[56]           References Cited

U.S. PATENT DOCUMENTS

| 4,071,694 | 1/1978  | Pfeiffer ........................................ 381/67 |
| 4,254,302 | 3/1981  | Walshe ..................................... 179/1 ST |
| 4,362,164 | 12/1982 | Little et al. ............................... 128/639 |
| 4,528,689 | 7/1985  | Katz ........................................... 381/67 |
| 4,528,690 | 7/1985  | Sedgwick .................................. 381/67 |
| 4,598,417 | 7/1986  | Deno .......................................... 381/67 |
| 4,731,849 | 3/1988  | Bloomfield, III .......................... 381/67 |
| 4,770,189 | 9/1988  | Shyu ......................................... 128/773 |
| 4,792,145 | 12/1988 | Eisenberg et al. ....................... 128/715 |
| 4,821,327 | 4/1989  | Furugard et al. .......................... 381/67 |
| 5,213,108 | 5/1993  | Bredesen et al. .......................... 381/67 |

*Primary Examiner*—Curtis Kuntz
*Assistant Examiner*—Vivian Chang
*Attorney, Agent, or Firm*—Baker & Botts

[57]              ABSTRACT

A combined electronic acoustical stethoscope having a compact conventional appearance is disclosed. The stethoscope includes a head assembly rotatably mounted on a spool and containing at least a diaphragm, a bell, a battery holder, a microphone, a speaker, signal processing means and, a programmable switch integrated with the spool. The microphone, speaker, signal processing means and programmable switch are concealed within the head assembly thereby providing the stethoscope with the compact conventional appearance.

15 Claims, 10 Drawing Sheets

COMBINED ELECTRONIC ACOUSTICAL STETHOSCOPE

BACKGROUND

1. Field of the Invention

This invention relates to diagnostic auscultation and in particular to a combined electronic acoustical stethoscope for recording and amplifying sounds produced by body structures.

2. Description of the Background

Auscultation has long been a very useful tool for medical diagnosis of ailments. By using a stethoscope, health care providers can listen and identify sounds associated with abnormalities. The most common of these are heart murmurs which, when properly identified, indicate specific abnormalities in the function of the heart. Identifying specific murmurs, like identifying heart sounds, is difficult. Developing the skills necessary to make a proper analysis takes years of study and practice. Since many heart murmurs are rare or seldom encountered by the general physician or medical students, expertise is never acquired. In addition, most of the body sounds fall either just at or below the audible frequency range of the human ear.

Modern electronic stethoscopes can improve sound quality and provide visual indication of heart sounds or chest sounds. However, these electronic stethoscopes are typically expensive and bulkier than conventional stethoscopes. Further, electronic stethoscopes typically require significant external electronics to operate. Accordingly there is a need for a stethoscope which combines the simplicity of a conventional stethoscope with modern electronics. The Echo+™ stethoscope offers modern electronics and digital recording techniques without significant changes to the external design or significant increase in cost.

SUMMARY OF THE INVENTION

This invention overcomes the problems and disadvantages associated with current strategies and designs and provides novel electronic stethoscope features for diagnostic auscultation.

One embodiment of the invention is directed to a stethoscope that receives and records a body sound while maintaining the standard stethoscope features. The stethoscope comprises a head with a bell end and a diaphragm end. The stethoscope contains a microphone, electronic circuits, a speaker, digital recording circuits and a means of eliminating acoustic feedback.

Another embodiment of the invention is directed to a method for amplifying and recording a body sound with a stethoscope. This method comprises placing a head of the stethoscope against a surface of a body. The body sound is detected by a microphone within the head of the stethoscope and processed. Body sounds are held in a digital recording circuit for playback.

Another embodiment of the invention is directed to a method for assembling a stethoscope that receives and records a body sound. The stethoscope is assembled by attaching a stethoscope head, that contains electronics (recording circuit, microphone, speaker, amplifier) to an elastic tube which connects the head to the ear pieces.

Other objects and advantages of the invention are set forth, in part, in the description which follows and, in part, will be obvious from this description, or may be learned from the practice of the invention.

DESCRIPTION OF THE INVENTION

As embodied and broadly described herein, the present invention is directed to novel electronic stethoscopes for diagnostic auscultation of body structures.

Conventional stethoscopes are designed to detect sounds produced in the body. A conventional stethoscope contains ear pieces connected to the bell/diaphragm by a flexible tube for receiving sound. This stethoscope is generally satisfactory and reliable but its simplicity is also a significant disadvantage as many physiological sounds are reproduced without sufficient clarity to perform rapid and accurate diagnosis of the physiological precursor of the sound.

The present invention comprises a conventional stethoscope and one that incorporates amplification and/or recording circuits possible with today's electronics. Electronic stethoscopes have been proposed to modify the physiological signal to produce an audible signal which has clarity and which more accurately reflects the original physiological sound. Some advantages and disadvantages of several such electronic stethoscopes are described in U.S. Pat. No. 4,528,689. In such stethoscopes, diagnostic resolution is improved, treatment and intervention techniques can be better assessed and there is minimal patient inconvenience. Many health care providers are accustomed to the conventional stethoscope and find electronic stethoscopes expensive, cumbersome, and difficult to use. However, the preferred embodiment of the present invention, the Echo+™ stethoscope, maintains all the classic features of a conventional stethoscope. In addition, the unit is capable of automatically adjusting the intensity of the auscultated sounds to optimize proper analysis by the user. The unit also captures (records) auscultated sounds which can then be replayed. These recorded sounds, can be replayed in one of two modes. The first mode reproduces the sounds just as recorded, thus allowing repeated analysis by several users. The second mode plays the recorded sounds back at a reduced rate, thus optimizing their analysis. The recording feature of the Echo+™ is especially useful when examining easily distressed patients such as the crying neonate. By capturing the auscultated sounds before the patient becomes irritated a more accurate analysis can be performed.

DESCRIPTION OF THE INVENTION

The recording feature offered by the Echo+™ also provides a practical and convenient method of assessing patient progress. By comparing pre-treatment and post-treatment auscultated sounds the Echo+™ can be used to gauge the success of treatment. In the teaching setting, the advantages for the student and patient are obvious. Students can replay the auscultated sounds over and over without repeatedly reexamining the same patient, thus minimizing patient inconvenience. Additional advantages offered by the Echo+™ stethoscope include transferring of information for consultation, capturing the most appropriate auscultation environment, maintaining the familiar classic features, improved murmur detection and analysis. In addition to the above, the Echo+™ offers improved conventional stethoscope resolution through improved acoustic chambers. The flexible metal conduit connects the housing to the ear pieces while maintaining a superior acoustic chamber. This conduit also maximizes external noise isolation and promotes self straightening and anti-kinking properties. The ear pieces have also been redesigned for better fit and longer useful life.

In the following detailed description of the preferred embodiment, reference is made to the accompanying drawings which form a part hereof, and in which is shown by way of illustration a specific embodiment in which the invention may be practiced. This embodiment is described in sufficient detail to enable those skilled in the art to practice the invention, and it is to be understood that other embodiments may be utilized and that structural changes may be made without departing from the scope of the present invention.

The stethoscope in according to the present invention is described in accordance with FIGS. 1–12. The preferred embodiment of the present invention looks substantially like a conventional stethoscope externally. In a preferred embodiment, locking ring/tensioner 44 is constructed of stainless steel. Construction of main body 35 is well known to those of ordinary skill in the art. Diaphragm plate 41 is preferably a standard epoxy diaphragm plate used in most new stethoscopes. Bell thermal isolator 42 and diaphragm thermal isolator 43 consist of a rubber ring stretched or molded over the stainless steel housing 80 is used to decrease thermal conduction and maintain a seal with main body 35. Main body 35

DESCRIPTION OF THE INVENTION is constructed from medical grade stainless steel and may be of standard construction which is well known in the art. Bell communication port 86 and diaphragm communication port 87 are circular holes in the main body positioned 180 degrees apart and are a standard part of the main body of many conventional stethoscopes. Spool socket 88 is preferably a circular hole into which spool 90 may be housed.

Microphone 205 is preferably an omni-directional electret condenser microphone element. Speaker 210 is preferably a standard miniature communications speaker. Electrical rotating connectors 400 are constructed of a nylon outer insulator 410 and brass conductors 420. Battery holder 110 is designed to hold battery 115, preferably a 6V lithium battery. Anti-twisting device 125 preferably consists of two independent stainless steel tubes and a rubber O-ring. Tubing 25 is preferably a bilumen (14"–16") neoprene tube. Neoprene is used to eliminate cracking and age induced stiffness related with conventional PVC and latex tubing. Compression spring 45 is preferably a standard stainless steel compression spring used to improve the acoustic chamber and to maximize external noise isolation.

Locking ring/tensioner 44 is constructed in such a way that it mates by screws or other suitable joining method to main body 35 and secures diaphragm 41 to main body 35 while maintaining a seal with the body 35. Locking ring/tensioner 44 increases or decreases the tension applied to the diaphragm plate 41 thus proportionally changing the resonant frequency of (or tuning) diaphragm plate 41. The locking ring/tensioner 44 also houses diaphragm thermal isolator 43 (which is a non-conductive rubber ring) to decrease thermal conduction transferred to the body. Bell thermal isolator 42 and diaphragm thermal isolator 43 are used to decrease thermal conduction and maintain a seal with the body.

The main body of the stethoscope is constructed from medical grade stainless steel and houses bell communication port 86 and diaphragm communication port 87, spool socket 88, microphone 205, speaker 210, electrical rotating connections 400, electronics 200. It should be understood that these component correspond to a particular embodiment of the present invention and other components may be substituted within the scope of the present

DESCRIPTION OF THE INVENTION invention. Bell communication port 86 and diaphragm communication port 87, are selected by the user by rotating spool 90, are positioned to provide through communication (e.g. a continuous air space) with the ear pieces 20 when in the conventional mode. In a preferred embodiment of the present invention the spool rotates independent of depression and release of spool 90. The diaphragm communication port 87 is in communication with microphone 205 when in the electronic mode. Spool socket 88 houses a stainless steel spring 70 and stainless steel ball bearing 67, which are used to lock the spool 90 into bell communication port 86 or diaphragm communication port 87. Bell communication port 86 or diaphragm communication port 87 are 180 degrees apart. Microphone 205 communicates with bell communication port 86 or diaphragm communication port 87 and provides input to the electronics. Speaker 210 is a standard miniature communications speaker that communicates directly with the user's ear canal when the user selects the electronic mode. Electrical rotating connectors 400 function as: 1-an on/off switch and 2-a connection between battery 115, housed in the battery holder 110, and the electronics 200 housed in main body 35.

The smart switch comprises the spool 90 and the electronics 200. When the spool is depressed the housing 35 and spool brass conductors 420 are aligned (making contact), which actuates the smart switch. If the connection is broken, without reconnecting within a few milliseconds, the unit returns to the conventional mode(off). If the connection is momentarily broken, i.e., depressing spool 90 two or three times in a row, the smart switch interprets the signal and selects the appropriate response (amplify/record, playback, slow playback).

Figure 8:
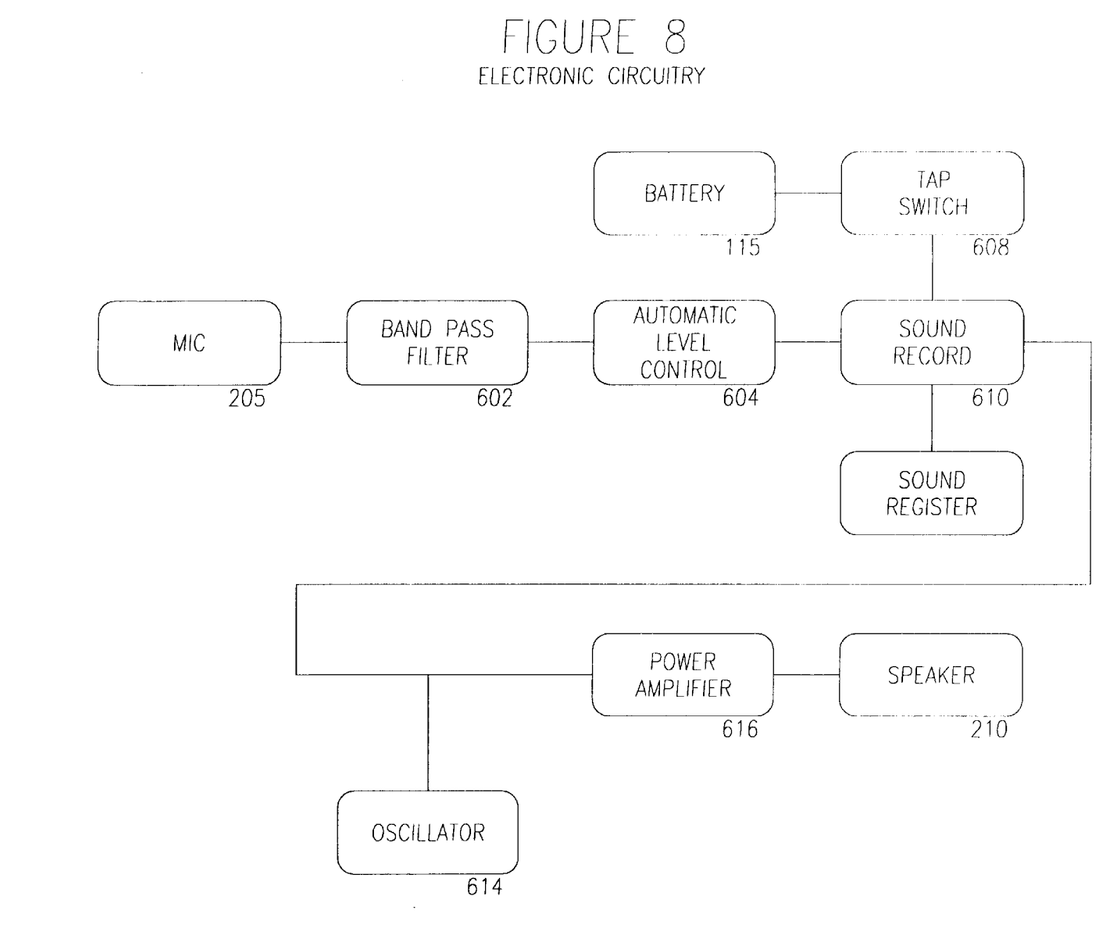
FIG. 8 A block diagram of the electronic circuitry.

FIG. 8 depicts one embodiment of electronic circuitry consisting of microphone 205, speaker 210, battery 115, and various electronic components. Electronics consist of band pass filter 602, automatic level control 604, sound recorder/sound register 610, tap switch 608, oscillator 614, and power amplifier 616. Electronics 200 (FIG. 5) are mounted and held in the stethoscope diaphragm. Band pass filer 602 limits the frequency of the signal from microphone 205 to a low pass of 70 Hz and a high pass of 480 Hz. Automatic level control 604 takes a given range of input signals and provides a constant level of AC output. Thus, a

DESCRIPTION OF THE INVENTION weak and strong heart will sound similar in amplitude. For example, if a patient is obese, the heartbeat sound may be dampened by excess fat between the heart and the stethoscope. In this case, automatic level control 604 operates to boost the signal level to the constant level, i.e., provides full gain. In contrast, when a patient is excessively thin, their heartbeat sound detected through the stethoscope may be very loud. In this situation automatic level control 604 operates to reduce the signal level to the constant level, i.e., provides minimal gain. Finally, when a stethoscope is in use, it may come into contact with objects, such as chest hairs, which cause loud "noise" signals. In this case, electronics 200 provide a muting function. Sound recorder/sound register 610 is a standard sound recording circuit which can record sound and play them back at variable speeds including normal speed. Sound recorder/sound register 610, in a preferred embodiment, has a storage capacity of 1,048,576 words×1 bit. Thus the worst case record time is approximately 14 seconds. Oscillator 614 generates a beep each time tap switch 608 is activated (e.g., positive position feedback). Power amplifier 616 increases the drive of the input signal such that it can drive speaker 210. Tap switch 608 decodes a series of activations (taps) into functions including amplified playback, and record. Tap switch 608 also controls the power to the other blocks in such a way as to save power (e.g., recorder is not powered up when in amplify mode).

Figure 5:
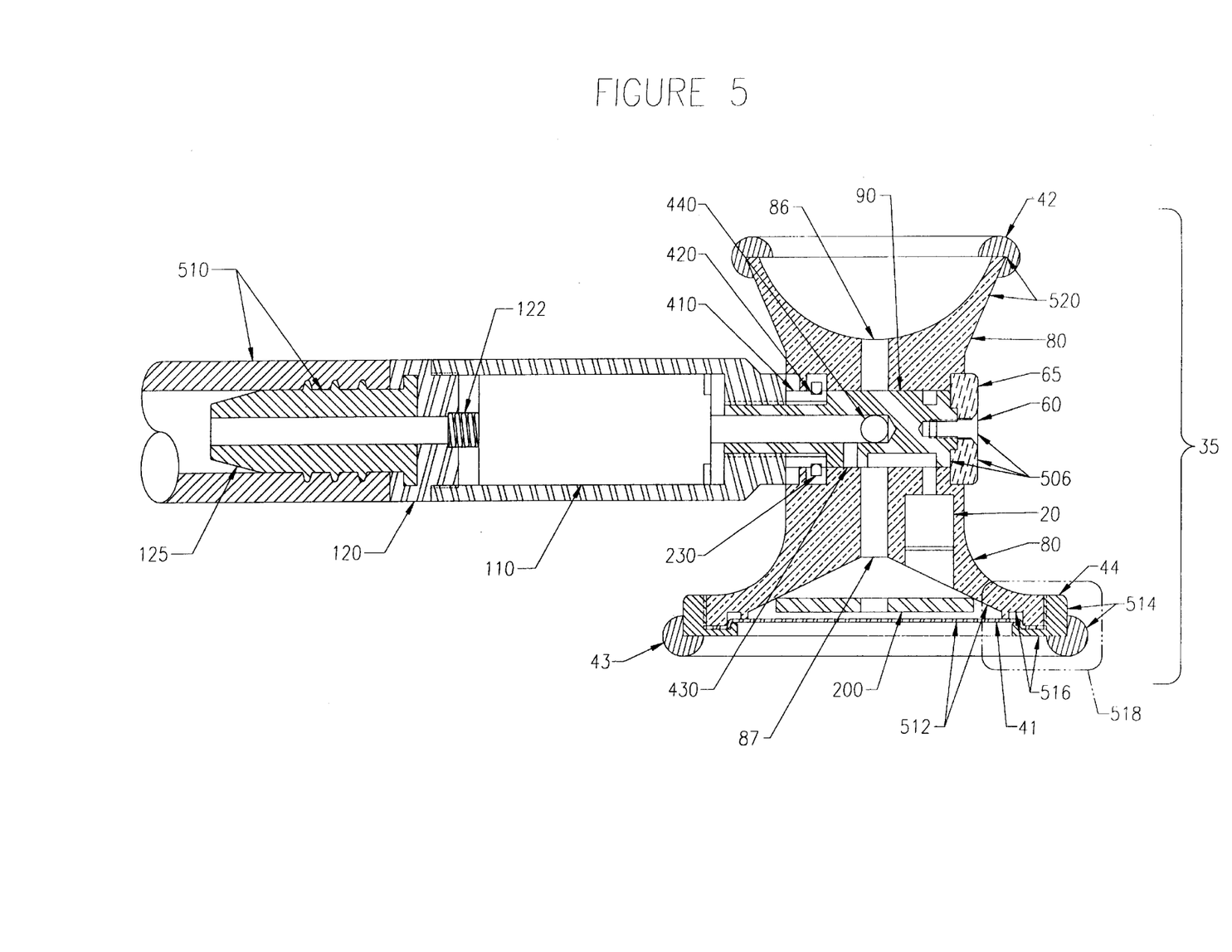
FIG. 5 A cross-sectional view of the stethoscope of a preferred embodiment of the present invention in electronic mode.
Figure 6:
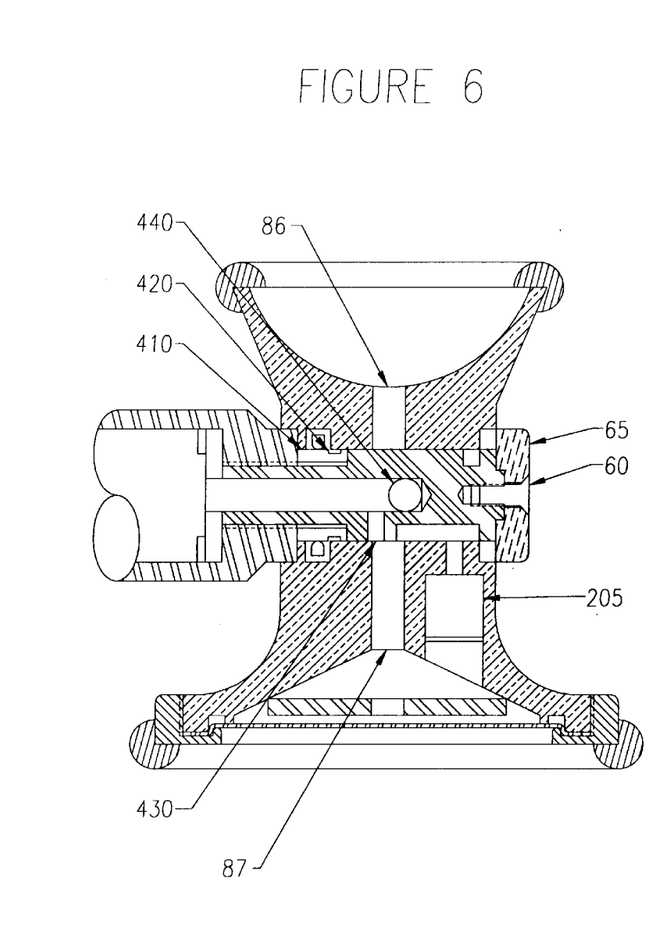
FIG. 6 A cross-sectional view of the stethoscope tube according to one embodiment of the present invention in conventional mode.
Figure 7:
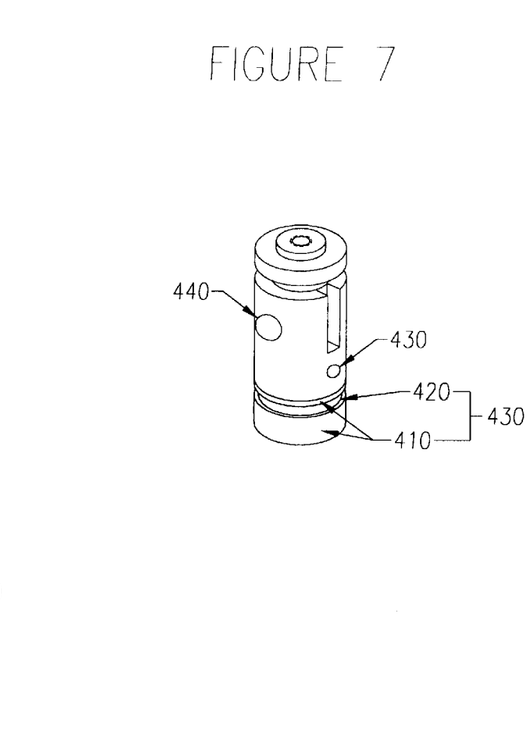
FIG. 7 A pictorial view of the spool of the present invention.

Referring to FIGS. 5, 6, and 7, the actuator spool 90 houses the through spool port 430, washer 65, screw 60, battery 115, spring 122 and rotating electrical connectors 400, battery retaining cap 120, speaker output 440, and anti-twisting device 125. Spool 90 may contain other components and remain within the scope of the present invention. Through spool port 430 is positioned in such a way that when spool 90 is in the conventional mode, direct connection with the ear pieces 20 exist. A female communication port (e.g., a quick connect female output jack 411) is incorporated into through spool port 86. Quick connect male output jack 700 provides a means of coupling the output of the stethoscope to an external device. When in the electronic mode (FIG. 5), the diaphragm communication port 87 is in communication with microphone 205. Speaker 210 is separated from the microphone 200, thus eliminating feedback, while maintaining a connection with the ear pieces. Battery holder 110 is designed to hold a 6V lithium battery and maintain a patent air canal. Battery holder 110 is shaped such that air can pass in the axial direction between battery holder 110 and main body 35. The user's ear canal is continuous with the air canal between the inside of the main body and the ear pieces. The user's ear canal is also continuous with the speaker 210 in the electronic mode (FIG. 5) and continuous with bell communication port 86 in bell mode or diaphragm communication port 87 diaphragm mode, when in the

DESCRIPTION OF THE INVENTION conventional mode (FIG. 6). A stainless steel spring 122 connected to the anti-twisting device 125 provides a compression force to hold the battery 110 into position. Anti-twisting device 125 preferably consists of two independent stainless steel tubes and a rubber O-ring constructed in such a manner that they can rotate independently while maintaining an air seal.

Figure 10:
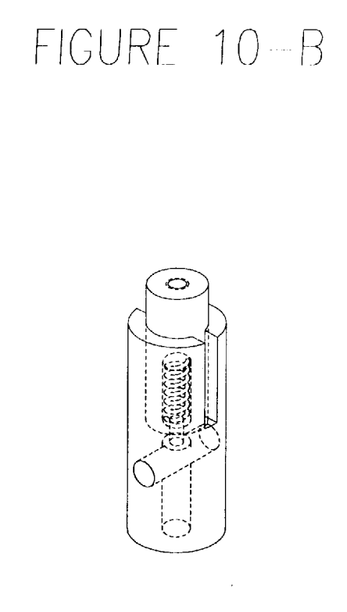
FIG. 10 pictorial and cross-sectional view of the spool plunger isolator
Figure 11:
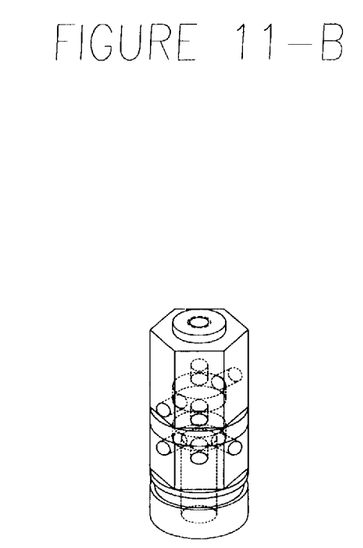
FIG. 11 pictorial and cross-sectional view of the spool hex isolator
Figure 12:
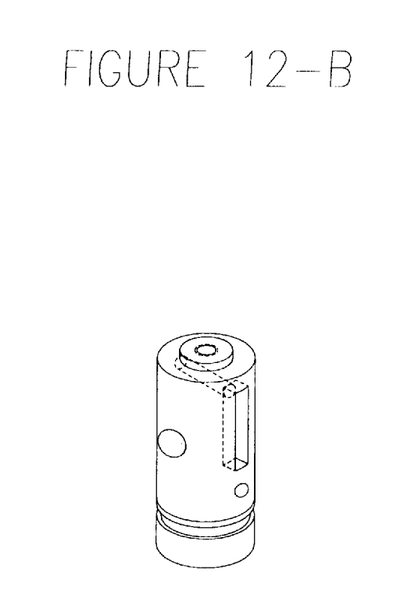
FIG. 12 pictorial and cross-sectional view of the spool slot isolator

In addition to the preferred actuator, spool 90, several different versions have been developed. Referring to FIG. 10, the first alternative, a spool plunger isolator, separates microphone 205 from speaker 210 and ear canal while maintaining a through connection with microphone 205. The through connection is selected by rotating spool 90, 180 degrees. When the plunger is depressed it closes the ear canal through port and eliminates feedback. When released the ear canal through port is free to communicate with the selected port. As with the current actuator, rotating the ear canal through port 180 degrees selects the bell communication port 86 or diaphragm communication port 87.

The second alternative, a spool hex isolator, (FIG. 11) separates microphone 205 from speaker 210 and ear canal while maintaining a through connection for microphone 205. The spool hex isolator consist of a hex with a distal blind hole and a proximal hole that connects with the tube. Direct connection between the blind port is through one side only. Depressing the actuator breaks the direct connection, thus isolating speaker 210 and microphone 205. Releasing the spool reestablishes communication between the ear canal and selected port. The remaining sides of the proximal hex port are used to provide a speaker through hole with the ear canal when in the bell or diaphragm mode. The remaining sides of the distal hex port are used to maintain a through hole with microphone 205 and selected port. Rotating the spool 180 degrees selects the opposite port.

The third alternative actuator, a fully automatic spool utilizing a miniature electric valve to separate the ports, has also been developed. This configuration eliminates the need to depress the spool to isolate various ports. When the electric valve is energized, speaker 210 and microphone 205 are separated while microphone 205 maintains communication with the selected port. The speaker maintains through communication with the ear canal. When the valve is not powered, direct communication with the ear canal and selected port

DESCRIPTION OF THE INVENTION exists. An alternative to the current spool configuration FIG. 7 is the spool slot isolator FIG. 12.

Figure 1:
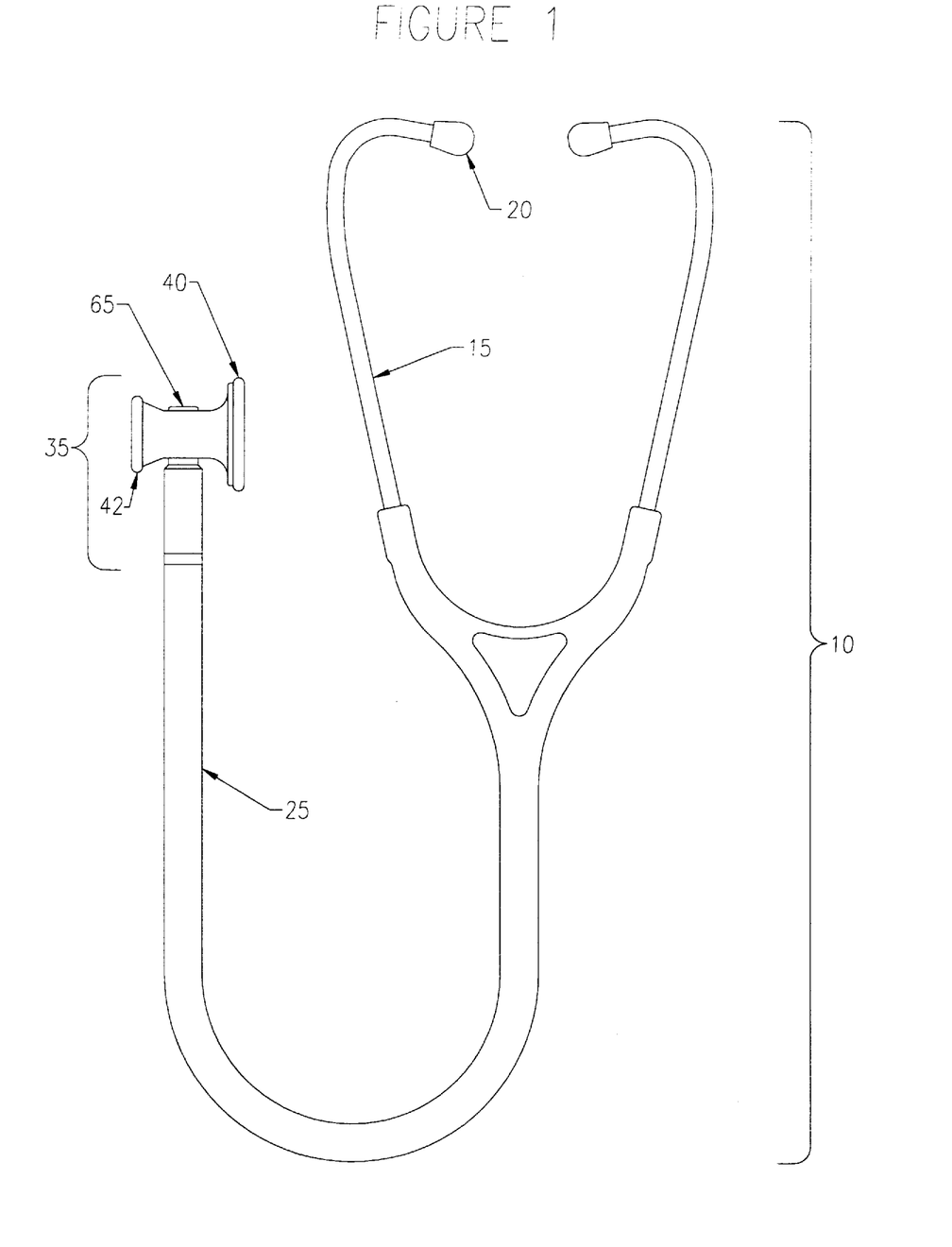
FIG. 1 A pictorial view of one embodiment of the present invention.
Figure 2:
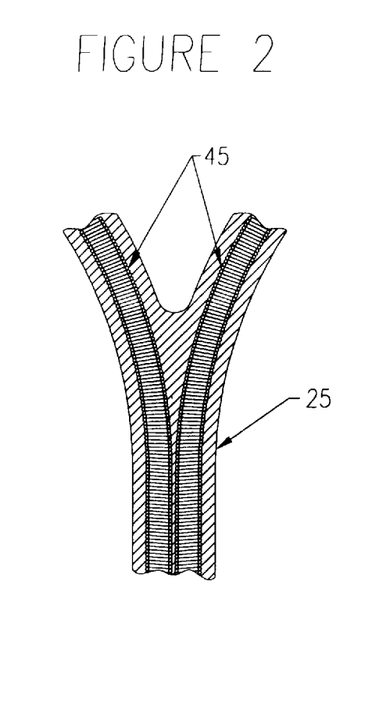
FIG. 2 A pictorial view of the stethoscope tube of a preferred embodiment of the present invention.
Figure 3:
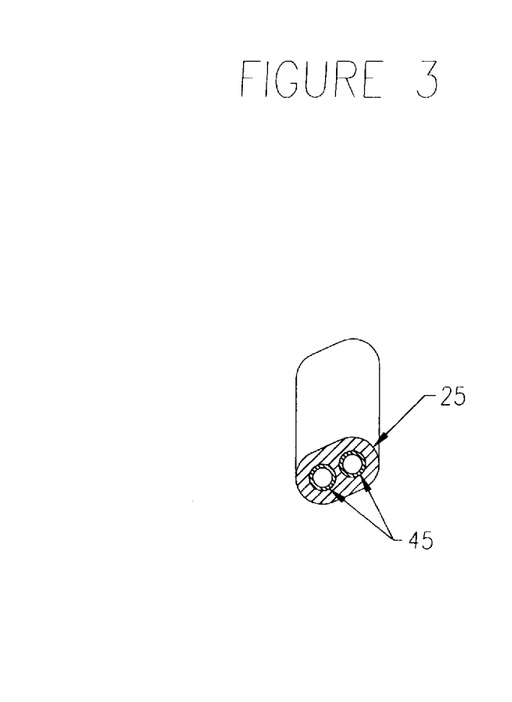
FIG. 3 A cross-sectional view of the stethoscope tube of a preferred embodiment of the present invention.

Referring to FIGS. 2 and 3, tubing 25 may be a bilumen (14"–16") neoprene tube. Neoprene is used to minimize cracking and age induced stiffness related with conventional PVC and latex tubing. In addition, a stainless steel compression spring 45 is molded into the tube 25 to improve sound transmission and prevent collapse of the tubing. The compression spring 45 also acts to straighten the tube when in use and maximize external noise isolation.

Elastic bodies have certain natural frequencies of vibration which are characteristic of the material and boundary conditions. When tube 25 and spring 45 are acted on by a series of periodic impulses, body cavity sounds, that have a frequency nearly equal to the natural frequency of the tube 25 and spring 45 they are set into vibration with a relatively large amplitude. Thus tube 25 and spring 45 configuration described maximize the phenomenon of resonance to provide a superior acoustic chamber. The configuration maximizes the loudness, pitch, and quality of the body cavity sounds while maintaining a flexible conduit to the ear canal.

Figure 4:
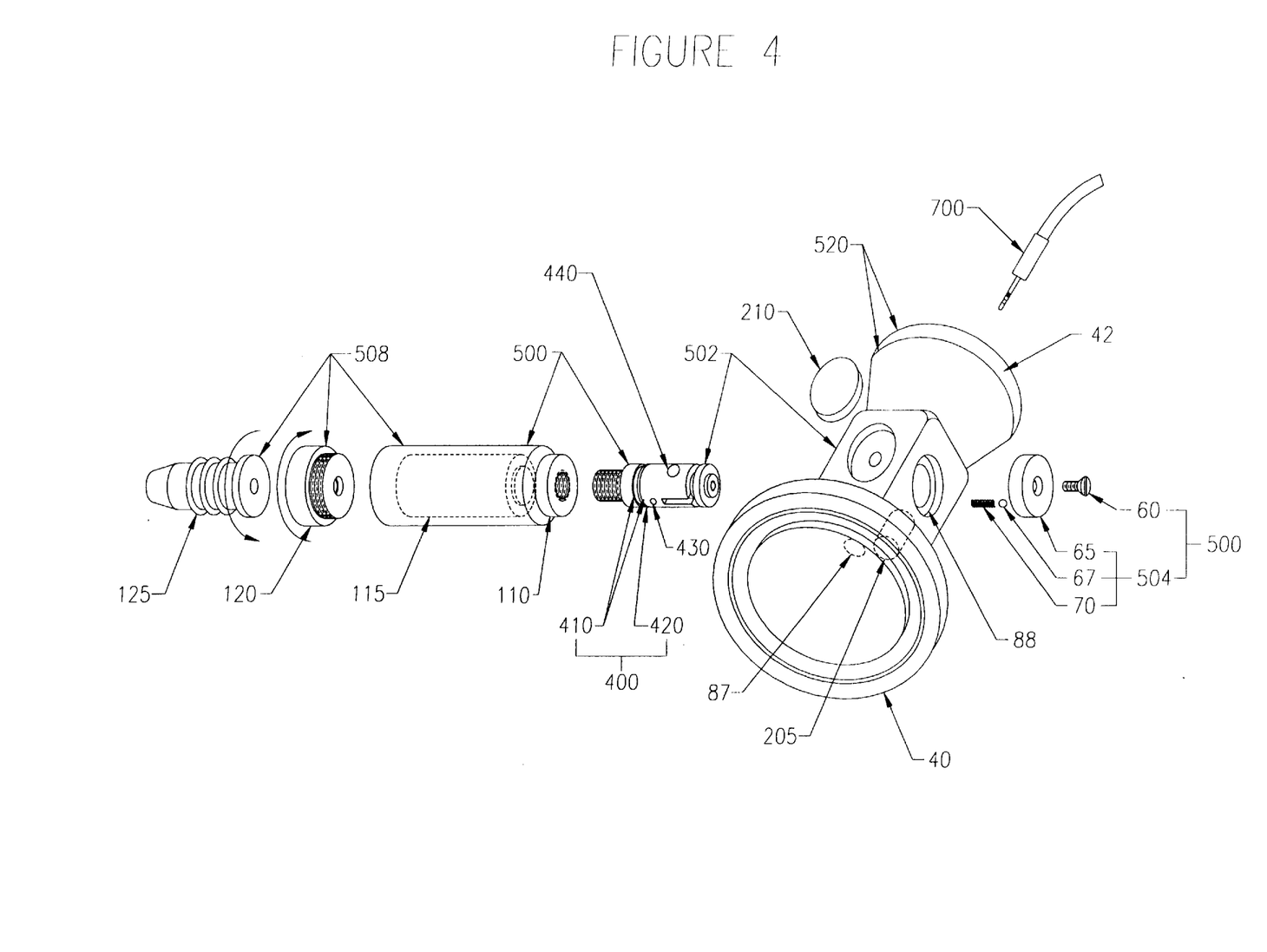
FIG. 4 A pictorial view of the apparatus representing the method of constructing a preferred embodiment of the present invention.
Figure 9:
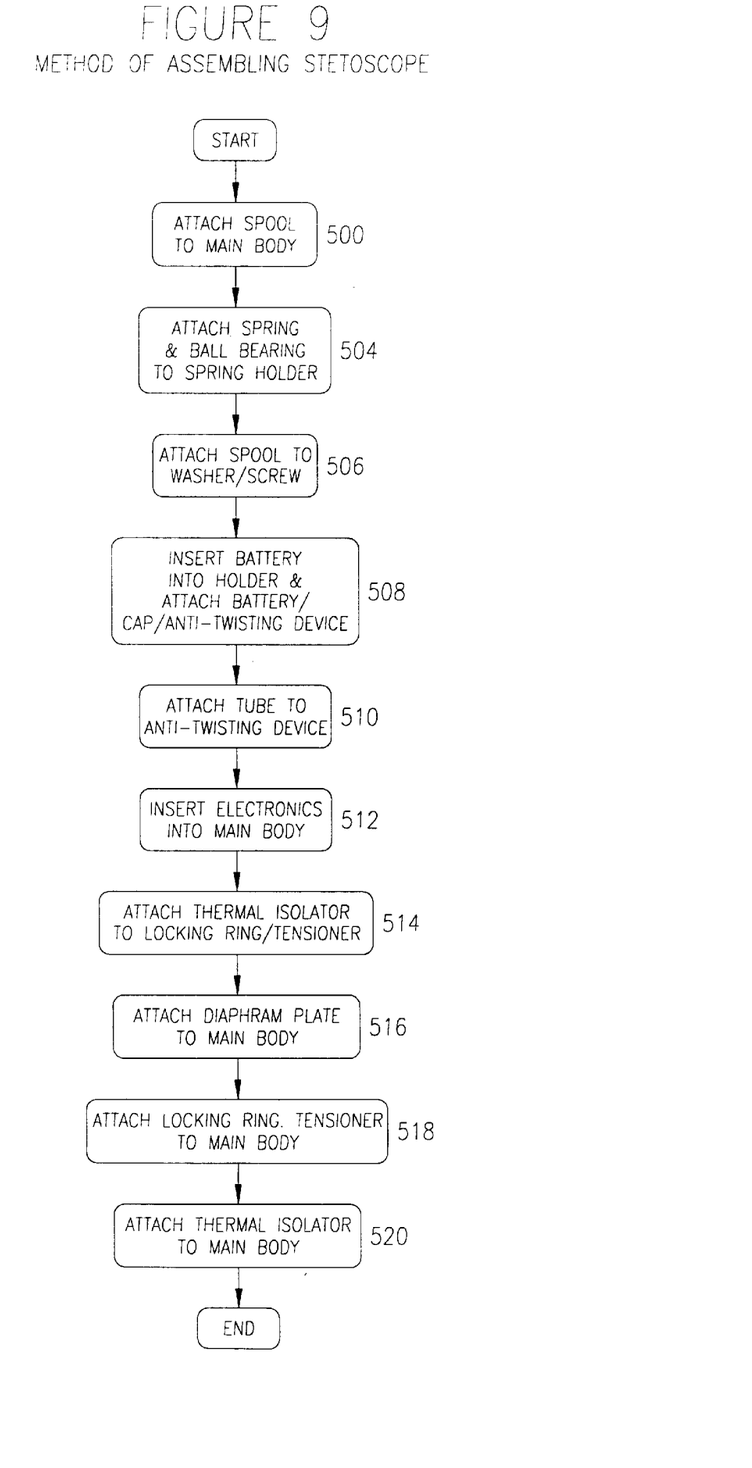
FIG. 9 A method of assembling a stethoscope of the present invention.

Referring to FIGS. 4, and 9, the stethoscope is assembled in a step wise sequence. Spool 90 is secured to battery holder 110. (step 500) Spool 90 with attached battery holder 110 secured into position is inserted into main body 35. (step 502) The spring 70 and stainless ball bearing 17 are placed into the spring holder (not shown). (step 504) Spool 90 is locked into position by washer 65 and screw 60. (step 506) Battery 115 is then inserted into battery holder 110 and secured into position by battery end cap 120 which is fixed to anti-twisting device 125. (step 508) Tube 25 is forced over the tapered barbed end of anti-twisting device 125. (step 510) Electronics 200 are inserted into their appropriate positions within main body 35 and secured into position. (step 512) Thermal isolator 42 is secured to locking ring/tensioner 44. (step 514) Diaphragm plate 41 is placed between the main body 35 and locking ring/tensioner 44. (step 516) Once aligned, the locking ring/tensioner 44 is secured to the main body 35. (step 518) Bell thermal isolator 42 is secured to main body 35. (step 520)

DESCRIPTION OF THE INVENTION

FIG. 5 depicts spool 90 and main body 35 in electronic mode. FIG. 6 depicts spool 90 and main body 35 in conventional mode. FIG. 7 depicts spool 90 in greater detail. Depressing the spool opens and/or closes bell communication port 87 in bell mode or diaphragm communication port 85 in diaphragm mode allowing the classic and electronic features to coexist without feedback.

Referring to FIG. 5, electronics 200 may be constructed of standard electronic chips or a combination of miniature hardware and software or other electronics suitable for performing the necessary functions within the given space limitations. Referring to FIG. 8, band pass filter 602 isolates pathological and physiological frequencies. Sound recorder/register 610 responds to tap switch 608 which includes an off, on#1, on#2, on#3 setting, which refers to off-amplify, playback, slow playback, and record respectively. Electronics 200 adapted for recording, allows for playback/slow playback of heart sounds while maintaining classic features of passive acoustic conduction. Each new recording will erase the previous recording.

The Echo+™ utilizes a hard flexible tube and three methods of noise reduction when in the electronic mode. Through electronics 200 the user is able to physically remove him or herself from a noisy environment. After recording, in a noisy room, the user can simply move to a quiet room for playback. The second method relies on the band pass filters in electronics 200 to attenuate frequencies above 470 Hz. Speech in the range of 2000 to 4000 Hz is filtered very effectively through the band pass filter. The third method of noise reduction makes use of destructive interference and superposition principles. This feature is available only in the real-time amplify mode. Through electronics 200, two different signals are produced. Signal one, consisting of pure body cavity sounds and external noise transmitted into the body cavity is filtered and amplified. A second signal representative of the external noise is inverted, filtered, and attenuated. The two signals are then allowed to destructively interfere with one another in the acoustic chamber. The net result of the destructive interference produces a third signal that represents pure body cavity sounds, i.e. unwanted noise is removed. This improved signal is transmitted to the ear canal through the flexible hard tube. Quick connect female output jack 86 allows

DESCRIPTION OF THE INVENTION playback of recorded heart sounds through external speakers or transmission over telephone lines. An embodiment of the present invention provides real time amplification in one unit that reproduces as exactly as possible at the users ear the sound pressure signals originating from a conventional diagram or bell type of chest piece. An additional embodiment utilizes a signal processing approach which adjust the amplifier gain control to improve diagnostic resolution. Microphone 205 detects audible sounds from patient and produces an output signal representative thereof and a variable gain amplifier 260 amplifies the output signals from microphone 205 to the speaker 210. The acoustic chamber, consisting of spring 45 and tubing 25 improves sound quality by providing less signal distortion and decay in signal amplitude than is typical experienced in conventional stethoscopes. Amplitude is maximized through resonance of spring 45 and tubing 25, thus providing less decay in amplitude than a conventional stethoscope when in conventional mode. Additionally, in slow playback the output is modulated to extend playback thus providing a slowed down version of the original sound, e.g. a slower heart beat without changing the quality of the sound as perceived by a health care provider. Other embodiments and uses of the invention will be apparent to those of ordinary skill in the art from consideration of the specification and practice of the invention disclosed herein. All U.S. patents and other documents cited herein are hereby specifically incorporated by reference. The specification and examples should be considered exemplary only with the true scope and spirit of the invention indicated by the following claims.

We claim:

1. A combined electronic acoustic stethoscope having a compact conventional appearance comprising:

a spool;

a spool communication port located in said spool;

a head assembly rotatably mounted on said spool, comprising:

a diaphragm;

a bell;

a battery holder;

a microphone;

a speaker;

signal processing means enabling a sound to be simultaneously recorded and monitored by a user; and, a programmable switch centrally located on top of said head assembly for selecting between a conventional mode in which said diaphragm and said bell are operative to receive sounds and acoustically transmit the received sounds to a user's ear through a continuous unimpeded air canal, and an electronic mode in which said microphone and said signal processing means operate to receive sounds and transmit the received sounds through the speaker;

said programmable switch and said spool integrated together such that by actuating said programmable switch said spool communication port opens and closes different acoustic ports within said head assembly;

said signal processing means controlled by said programmable switch;

said microphone, speaker, signal processing means and programmable switch concealed within the head assembly thereby providing the stethoscope with said compact conventional appearance;

a conduit assembly having a proximal end and a distal end, the proximal end of the conduit assembly connected to the spool; and, a first and a second ear piece connected to the distal end of the conduit assembly.

2. The stethoscope of claim 1 wherein the conduit assembly comprises:

a flexible outer tube made of a first material;

a first inner hard tube contiguous with an air column of a first acoustic chamber, said first inner hard tube independent from and disposed within said outer tube made of a second material, said second material being harder than said first material; and, a second inner hard tube contiguous with an air column of a second acoustic chamber, said second inner hard tube independent from and disposed within said outer tube made of the second material, said first and second hard tube defining said first and said second acoustic chamber respectively.

3. The stethoscope of claim 2 wherein said first and second hard tube comprise a spring.

4. The stethoscope of claim 1 wherein said diaphragm comprises a tunable diaphragm having a frequency response which is adjustable.

5. The stethoscope of claim 4 wherein said tunable diaphragm comprises:
- a diaphragm element; and,
- a tensioner rotationally coupled to said diaphragm element;
- whereby rotating the tensioner adjusts the tension in said diaphragm element.

6. The stethoscope of claim 1 further comprising:
- a bell communication port located in said bell; and,
- a diaphragm communication port located in said diaphragm;
- wherein in the acoustic mode, the head assembly rotates to align the bell communication port or the diaphragm communication port with the spool communication port to form the continuous unimpeded air canal.

7. The stethoscope of claim 6 further comprising a quick connect output jack located within the bell communication port.

8. The stethoscope of claim 1 wherein said signal processing means is operable to detect, amplify and record a sound.

9. The stethoscope of claim 1 wherein the signal processing means comprises a digital recording circuit.

10. The stethoscope of claim 1 wherein the signal processing means comprises a band pass filter.

11. The stethoscope of claim 1 wherein the signal processing means comprises a digital sound recorder and a digital sound register operative to record a received sound and play the sound back at one of a plurality of speeds.

12. The stethoscope of claim 1, wherein the signal processing means comprises an automatic level control circuit operative to receive an input signal having a level within a given range and produce a constant level output signal.

13. The stethoscope of claim 1, wherein the signal processing means comprises power amplifier operative to increase the level of the input signal to a level sufficient to drive the speaker.

14. The stethoscope of claim 1, wherein the programmable switch comprises an oscillator operative to produce an audible indication of the selected mode.

15. The stethoscope of claim 1 further comprising an anti-twisting device positioned between the spool and the conduit assembly, said anti-twisting device enabling the head assembly, the spool and the conduit assembly to be independently rotated.

* * * * *